United States Patent [19]

Sampson et al.

[11] 4,289,029
[45] Sep. 15, 1981

[54] HIGH TEMPERATURE INJECTION AND VAPORIZATION SYSTEM FOR GAS CHROMATOGRAPHY

[75] Inventors: Robert W. Sampson, Arlington Heights; Francis H. Franke, Elk Grove Village, both of Ill.

[73] Assignee: UOP Inc., Des Plaines, Ill.

[21] Appl. No.: 90,818

[22] Filed: Nov. 2, 1979

[51] Int. Cl.³ ............................................. G01N 1/14
[52] U.S. Cl. ............................ 73/863.11; 73/863.84; 73/864.81
[58] Field of Search .......... 73/422 GC, 422 TC, 23.1, 73/61.1 C

[56] References Cited

U.S. PATENT DOCUMENTS

| 3,137,174 | 6/1964 | Hawk et al. |
| 3,306,502 | 2/1967 | Harris, Jr. |
| 3,482,450 | 12/1969 | Harris, Sr. et al. ............ 73/422 GC |
| 3,508,442 | 4/1970 | Lightner et al. |
| 3,631,724 | 1/1972 | Oster et al. |

4,124,358 11/1978 Muller .............................. 73/61.1 C

FOREIGN PATENT DOCUMENTS 412546 9/1974 U.S.S.R. ......................... 73/422 GC

Primary Examiner—S. Clement Swisher
Attorney, Agent, or Firm—James R. Hoatson, Jr.; Barry L. Clark; William H. Page, II

[57] ABSTRACT

Sample injection and vaporization system for gas chromatography is capable of continuous injection of a liquid hydrocarbon sample in the −44° F. to 1074° F. boiling range from a closed system such as a flowing liquid stream or high pressure sample bomb. The system overcomes the temperature limitations inherent in the seals of existing sample valves and utilizes a syringe to transport a liquid sample from the sample stream to a hot vaporization zone through which a carrier gas is flowing. Insulating means keep the sample block containing the seals, including one which is contacted by both the carrier gas and sample stream, at a sufficiently low temperature to protect the seals.

11 Claims, 7 Drawing Figures

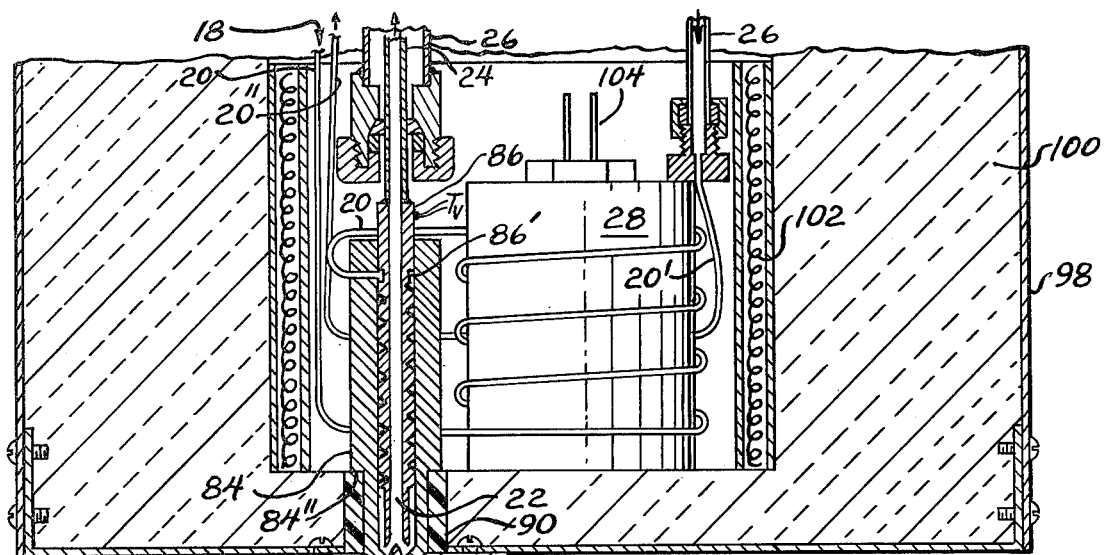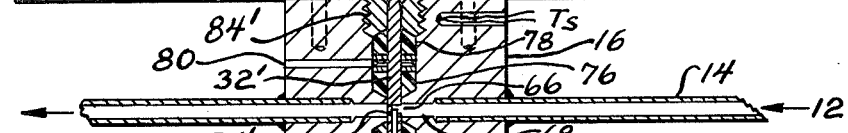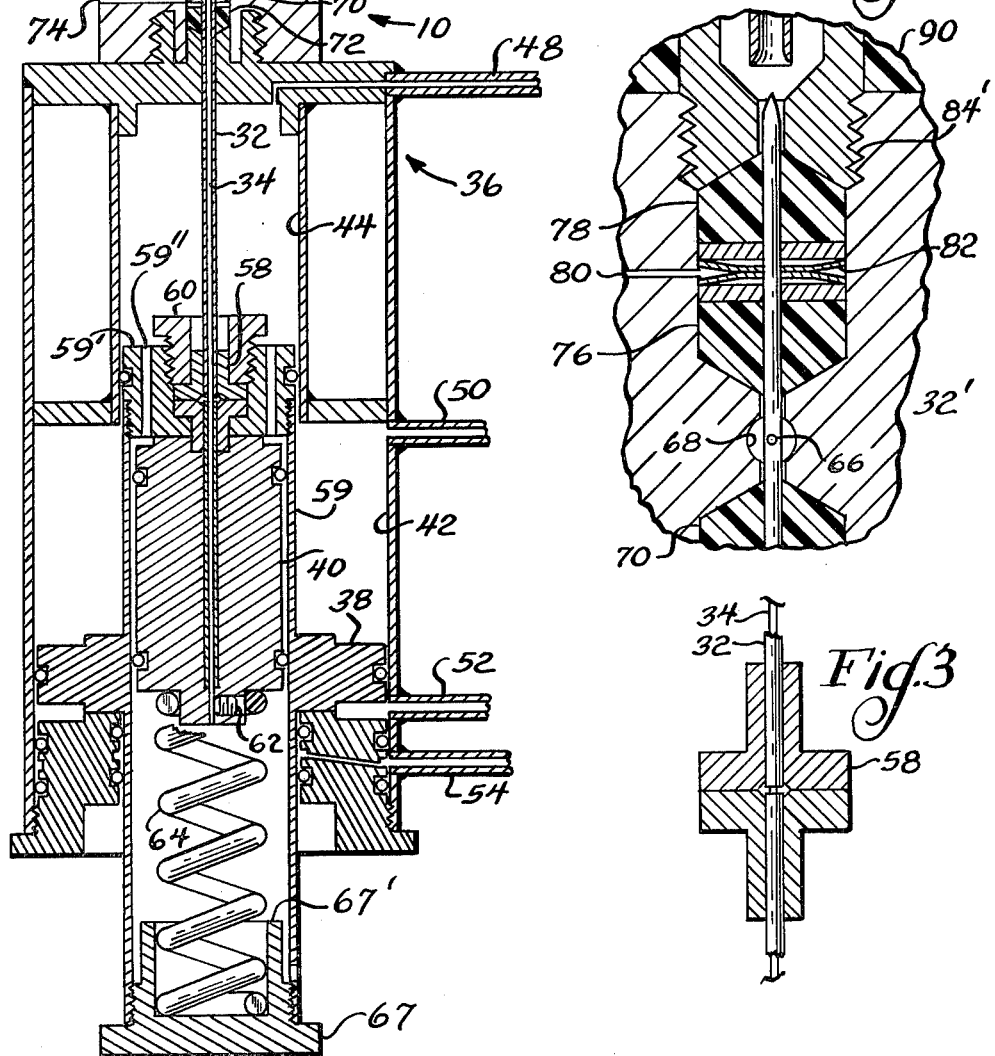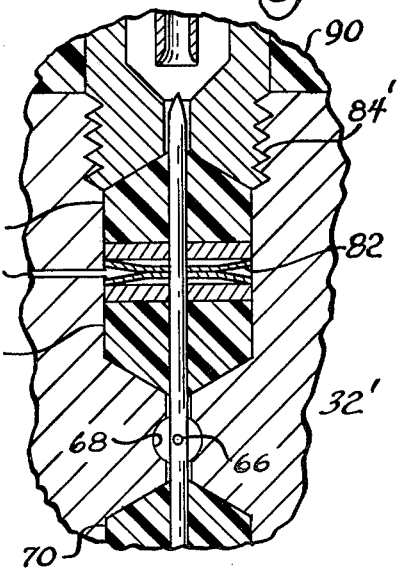

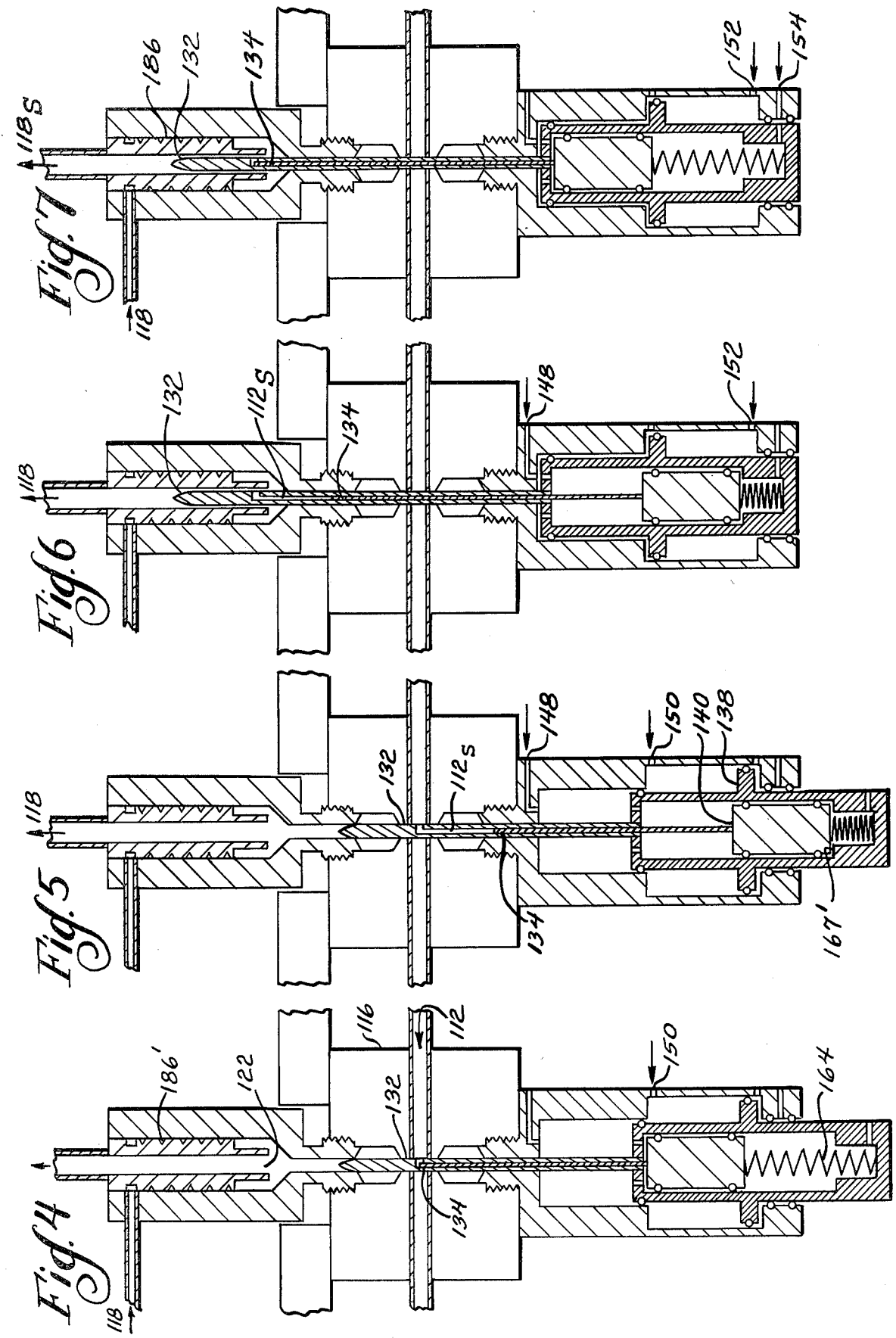

HIGH TEMPERATURE INJECTION AND VAPORIZATION SYSTEM FOR GAS CHROMATOGRAPHY

BACKGROUND OF THE INVENTION

In gas chromatography, it is often necessary to repeatedly inject a representative portion of a sample. The sample must be reproducibly introduced into a moving gas stream at pressures and temperatures well above ambient. Current injection systems consist of a hand held syringe or liquid sample valve which must deliver a reproducibly metered volume of sample in liquid form into an injection port or vaporizer. The injection port or vaporizing device volatilizes the liquid sample and entrains it in the flowing carrier gas stream which subsequently moves it to the separation column. The liquid must be volatilized in as short a time as possible; thus it is necessary to sufficiently heat the vaporization area and at times the carrier gas to rapidly flash the sample.

The hand syringe injection of a sample consists of first loading the syringe with a volume of sample by withdrawing the plunger. Next, the syringe needle is pushed through the septum, a small silicone rubber disc, of the injection port, and the plunger is depressed to discharge the sample by positive displacement into the injection port vaporization area. Finally, the syringe is withdrawn from the septum. The septum is the only barrier between the chromatographic process and the outside environment.

Where a liquid sample valve is used, the valve is generally heated and may be of the rotary, sliding plate or other types, consisting of a fixed volume sample loop or cavity through which liquid sample is generally flowing under pressure. When the valve is indexed to the sample inject position the liquid volume trapped in the sample loop or cavity is vaporized. Vaporization takes place by flashing the material in the carrier gas port of the heated sample valve or built in heated vaporizer while the material is exposed to a flowing carrier gas stream.

Both of the aforementioned systems are limited by temperature and to varying degrees by pressure, loss of light material or incomplete vaporization of heavy ends of the sample.

The hand syringe injection system, besides not being continuous, suffers from loss of light material present in full boiling range samples. The syringe and sample have to be heated at atmospheric pressure to a point where the material is fluid enough to load and displace from the syringe. Liquid in the needle tip may be prematurely forced out by thermal expansion when the needle enters the hot septum, thus depositing some material onto the septum which may later gradually release and interfere with the current and/or later sample results. Both of these effects can be observed when comparing the results of sampling with closed and open systems.

The septum must be changed daily because repeated puncturing will eventually destroy its mechanical strength which results in carrier gas leakage. If close attention is paid to the septum area upon withdrawal of the syringe, some vapors can be observed either exiting from the syringe needle or leaking momentarily from the septum, due to the pressure and high temperature required at the injection port to volatilize the liquid. This results in loss of material and varying sample volume.

An attractive feature of a syringe is the positive displacement of the liquid into the vaporization area, as compared to the heated sample valve. The sample valve relies on the sample loop or cavity to be at a sufficiently high enough temperature to flash volatilize the liquid so that it can be flushed out by the carrier gas. If the sample valve cannot be kept at a high enough temperature, some of the material, generally heavies, will remain in liquid form on the inner surface of the sample loop or cavity, thus preventing a correct analysis of the sample.

To minimize loss of light sample components and achieve repeatable sample volume injection the liquid sample valve with its metered flow through sample loop or cavity under pressure is definitely better than the hand held syringe. However, wider boiling range liquids require increased valve temperature to vaporize the liquid and increased pressure to maintain the light components as a liquid until time for injection. This prevents dual phase sampling which results in variable sample volumes.

The temperature and pressure at which a sample valve can be maintained on a continuous basis is limited by the valve's materials of construction. Present state of the art valves have a maximum continuous operating temperature of about 400° F. at which point the seals begin to deform and the valves begin to leak. This limits the liquid sample which can be successfully injected to those with end points below 750° F. Some manufacturers have valves they claim operate at about 660° F. but investigation indicates that the valves do not operate on a continuous basis or for very long.

In the art of liquid chromatography, a syringe type injection system is disclosed in Oster et al. U.S. Pat. No. 3,631,724. The syringe is reciprocable in a block wherein it is engaged by a pair of spaced seals positioned to either side of a channel containing the carrier liquid. A portion of the syringe always remains in the carrier stream so as not to propagate a pressure surge. One end of the syringe has an opening at its end or in an adjacent portion of its side wall into which a measured dose of a liquid sample may be sucked by an internal piston when the syringe tip has a container of liquid brought into contact with it.

SUMMARY

It is among the objects of the present invention to provide an injection system for a gas chromatograph that will permit continuous injection of liquids into a carrier gas stream which have boiling points much higher than can be accommodated with existing systems.

The invention basically involves the use of an automatic septumless injection syringe which: (1) draws a sample in liquid form from a flowing liquid stream under moderate temperature and pressure; (2) by positive displacement injects the liquid sample into a heated vaporization zone where it is volatilized and entrained in a flowing carrier gas stream from which is is subsequently delivered to the column inlet of a gas chromatograph.

The injection syringe is mounted in a pneumatic drive which consists of inner and outer pistons and cylinders into which compressed air is fed. Operation of air solenoid valves, preferably under the control of a microprocessor in a specific sequence, draws the liquid sample into the syringe, moves the syringe needle into the vaporization zone, displaces the liquid sample, and withdraws the syringe needle. The vaporization zone is attached in sealed relation to the sample block in axial alignment with the syringe and pneumatic drive. The sample block preferably consists of a stainless steel block which is cross bored to allow sample to flow through and across the syringe needle while a lateral opening in the syringe needle is moved in and out of the sample stream. The seal between the chromatographic process and the sample stream is made by means of a packing gland which is compressed against the outer wall of the syringe needle and a tapered cavity in the sample block.

The injection sequence begins with compressed air slowly moving the inner piston back, thus moving the syringe plunger back so as to load the syringe needle through the lateral opening with liquid sample under pressure. Next, compressed air moves the outer piston, placing the lateral opening of the needle in the vaporization zone. The pressure is then applied to the opposite side of the inner piston so as to move the plunger forward and displace the liquid into the vaporization zone. The injection sequence ends when the pressure is applied to the opposite side of the outer piston which returns the lateral opening in the syringe needle to the reset position in the flowing liquid stream.

The vaporization zone consists of an outer and inner section made from either stainless steel tubing or solid rod with a short piece of tubing extending from the top which penetrates the chromatographic column packing. The three pieces are fitted together and silver soldered or welded in place.

The inner section is hollow with three spiral grooves cut in the outer wall of its main body portion while the end portions are smooth. The multiple grooves serve to insure a more uniform flow to the injection zone. The outer section serves to mount the inner section and also as a heat sink and includes a side entrance for the carrier gas. The lower end of the outer section is screwed into the sample block and a pressure seal between the chromatographic process and the sample stream is produced by compressing a packing gland against the outer wall of the syringe needle and the inner wall of a cavity in the sample block.

After the carrier gas enters the vaporization zone it is partially heated while spiraling down between the two sections. Exiting the spirals the flow continues uniformly down the outer surface of the annular area and then up the center, exiting the vaporization zone and onto the chromatographic column. At the time of sample injection the lateral opening of the syringe needle automatically moves up and well within the inner section of the vaporization zone. The liquid sample is then injected by positive displacement and flash vaporized. The sample vapors are entrained in the flowing carrier gas and subsequently move to the column to be chromatographed.

The uniqueness of the invention comes from the fact that continuous automatic septumless syringe injection and vaporization can be made with liquid hydrocarbon samples in the $-44°$ F. to $1074°$ F. boiling range from a closed system, such as a flowing liquid stream or high pressure sample bomb, with little or no loss of light material.

As long as the $-44°$ F. to $1074°$ F. sample can be homogenously liquified, it can be injected, vaporized and chromatographed. This has been verified by injection of normal paraffins blends of $nC_4$ through $nC_{44}$.

BRIEF DESCRIPTION OF THE DRAWINGS

FIG. 1 is a front sectional view illustrating the improved injection system in operative association with a gas chromatograph column and detector;

FIG. 2 is a side sectional view and an enlargement of the upper seal portion of the structure of FIG. 1;

FIG. 3 is an enlargement of the needle support structure shown in FIG. 1; and

FIGS. 4-7 are somewhat schematic views illustrating the progression of steps involved in loading the syringe of FIG. 1 with a sample and injecting it into the carrier gas.

DESCRIPTION OF THE PREFERRED EMBODIMENT

Referring to FIG. 1, the improved sample injection system is indicated generally at 10. The system is adapted to be used with a liquid sample stream 12 which is passed through a length of sample tubing 14 into a sample block 16. Within block 16, a small volume of sample is captured from the sample stream for injection into a carrier gas stream 18 in a manner to be hereinafter described. The carrier gas stream 18, typically helium, is passed into a length of carrier gas tubing 20 which is directed, for the purpose of heating the gas, in a somewhat tortuous path into a vaporization zone 22 where the small captured sample from the sample stream 12 is injected into it. The vaporized sample is then directed through a tube 24 into a chromatographic column 26. The sample is separated into its various components in the usual manner within the column 26 and then exits the column through tubing 20' into a detector block 28 where the different components are sensed before the carrier gas exits the apparatus through tubing 20''.

Injection of the sample is accomplished by a syringe needle 32 which is hollow throughout its length except for a solid tip portion 32'. A plunger 34 is mounted within the hollow needle 32 and includes a tip portion 34' which normally fills the space behind the solid tip 32' but which can be drawn downwardly in the needle portion 32 away from the solid tip 32' in order to collect a measured volume of the sample stream 12. Movement of both the syringe needle 32 and the plunger 34 are accomplished by the piston and cylinder assembly indicated generally at 36. This assembly includes an outer needle control piston 38 and an inner plunger control piston 40. The pistons cooperate, respectively, with an outer cylinder portion 42 and an inner cylinder portion 44. Movement of the pistons within their respective cylinders is accomplished by causing air to enter one or more of the air tubes 48, 50, 52 and 54 in a desired sequence as will later be described in connection with FIGS. 4-7. The syringe needle 32 is firmly engaged in a holder portion 58 which is shown on a larger scale in FIG. 3. The holder portion 58 is mounted in the upper end portion 59' of a vertically moving tube 59 which is shown as being integral with the needle control piston 38 but which could be formed separately and attached mechanically to the piston. The plunger 34 is anchored to the plunger control piston 40 by means of a set screw 62. The plunger control piston 40 is normally biased to the upper end of the cylinder 59 by a spring 64. When it is desired to withdraw the plunger 34, a charge of air is brought in through tube 48 and through axial openings 59'' into communication with the top end of piston 40 which will be driven downwardly against the force of the spring 64.

A sample is drawn into the syringe needle 32 through an aperture 66 which is formed in the side of the needle at the lower end of the needle tip 32'. When the needle 32 is in the position shown in FIG. 1, the aperture 66 is in communication with the sample stream 12 present in the flow channel 68 within the block 16 so that withdrawal of the plunger 34 will draw a predetermined quantity of sample into the needle. The size of the sample is determined by the stroke length of the piston 40 and the inside diameter of the needle 32. A shoulder 67' on a replaceable end cap 67 contacts the lower end of plunger piston 40. To change the sample volume, one need merely replace the cap 67 with one having a longer or shorter shoulder extension 67'. Since the needle 32 must be movable upwardly so that the sample drawn into hole 66 may be ejected into the vaporization zone 22, a series of seals are provided to prevent leakage either to or from the piston and cylinder assembly 36 or to or from the vaporization zone 22. A pair of axially spaced lower seals 70, 72 are positioned between the flow channel 68 and the piston cylinder assembly 36 and a vent 74 is provided between the seals in a double block and bleed arrangement. In this arrangement, any leakage of the sample past seal 70 will be vented at 74 so that it cannot leak into the assembly 36 and likewise, any leakage from the assembly 36 past seal 72 will be vented before it can reach the sample stream. A similar arrangement is provided between the flow channel 68 and the vaporization zone 22 and includes seals 76 and 78 which are preferably made of Teflon and a vent 80 between them. The latter structure is shown in more detail in FIG. 2. In order to prevent the need for any adjustment of the seals 76, 78 to accommodate wear or manufacturing tolerances, for example, a spring means such as a pair of Belleville washers 82 are provided between the seals to continually apply an axial pressure to them.

The vaporization zone 22 lies within an outer tube-like member 84 which has a necked-in lower tip portion 84' threaded into engagement with the sample block 16. Positioned inside the outer tube portion 84, and preferably silver soldered thereto is an inner tube portion 86 which has a three start spiral groove 86' around its exterior and in contact with the inner wall of the outer tube 84. A shoulder portion 84" separates the narrow end portion 84' from the main body portion 84 and forms a seat for an annular insulating ring 90. The necking down of the lower portion of the tube 84 significantly reduces the amount of heat which may be conducted from the normally hot upper end of the tube down to the sample block 16. Conductance of heat is further limited by means of the insulating ring 90 and by the cooling effect of the helium gas which expands by the fact that its pressure falls from about 20 psig to about 2 psig as it enters the vaporization zone. Additional isolation of the heat in the vaporization zone to prevent it from reaching the sample block 16 is achieved by the housing 98 which contains insulation 100. The insulation is positioned around and under the heater coils 102 so that the heat will be concentrated in the region of the detector block 28 and the tubes 84, 86 in which the carrier gas 18 is preheated before it is contacted by the injected sample in the vaporization zone 22. The detector block 28, which may be of the thermoconductivity diffusion type, for example, preferably contains a detector filament assembly 104 which is not shown in detail but which typically comprises a heated filament which is contacted by the carrier gas and is arranged along with a detector reference filament and two fixed resistors in a Wheatstone bridge circuit. The conductance of the gas contacted filament varies with changes in temperature but is constant when pure carrier gas is exiting the chromatographic column 26 through tubing 20', thus causing the bridge circuit to be in equilibrium. However, when the discrete components of the hydrocarbon sample, which are separated in the column 26, contact the detector filament, sequential heating takes place as a result of thermoconductivity changes. This results in a sequential unbalance of the bridge circuit which can be sensed in an appropriate manner such as by a strip chart recorder which will draw a peak away from its base line as each hydrocarbon component is detected. The area of the peak for each component will be indicative of the percentage amount of that component in the sample stream.

To make the disclosed system capable of separating a liquid hydrocarbon sample containing a full range of materials from $C_4$–$C_{44}$ in the $-44°$ F.–$1074°$ F. boiling range, the heater 102 must cause the inner tube 86 to reach a temperature of about $600°$–$650°$ F. Where helium is used as the carrier gas 18, such a temperature is sufficient to vaporize any liquid within the range which contacts the inner walls of the tube 86 since a $C_{44}$ hydrocarbon which boils at atmospheric pressure in air at about $1000°$ F. will boil in the slightly pressurized helium in the vaporization zone 22 at a temperature of about $580°$ F. In the embodiment depicted in FIG. 1, where the temperature of the vaporization zone measured at $T_v$ was $650°$ F., the temperature of the interior of the sample block at $T_s$ was only $200°$ F. Thus, the seals 76, 78 are very well protected from being damaged by excessive temperatures.

FIGS. 4-7 are somewhat simplified representations which illustrate the positions of the various elements of the improved injection system of FIG. 1 during the injection cycle. The reference characters 110-186 are meant to refer to elements which correspond to the elements numbered 10-86 in FIG. 1.

In operation, the carrier gas 118 passes in the direction of the arrow continually through the grooves 186' and up through the vaporization zone 122 toward the chromatographic column. The liquid 112 to be sampled passes continually through the sample block 116. When the plunger 134 is withdrawn from its FIG. 4 to its FIG. 5 position by the introduction of air to ports 148, 150, a liquid sample $112_S$ is drawn into the space within needle 132 vacated by the plunger. The sample is then carried upwardly to its FIG. 6 position by providing air to ports 148 and 152. Once in the FIG. 7 position with the carrier gas 118 swirling upwardly around the needle 132, air supplied to ports 152, 154 causes the sample to be injected into the gas 118 and immediately vaporized by contact with the warmed gas and the heated walls of the inner tube portion 186 of the vaporization zone. The vaporized sample $118_S$ then leaves the vaporization zone and enters the chromatographic column (not shown). After injection, the syringe needle and plunger are returned to their FIG. 4 position by introducing air to inlet 150. As can be seen in the various figures, introduction of air to inlet 150 will drive the piston 138 and needle 132 downwardly while application of air to inlet 152 will force them upwardly. Similarly, introduction of air to inlet 148 will force the piston 140 and plunger 134 downwardly while application of air to inlet 154 will force them upwardly. The spring 164 biases the piston 140 upwardly in the FIG. 4 position when inlet 154 is out of communication with the piston.

We claim as our invention:

1. A gas chromatograph injection system for injecting a measured sample of fluid from a relatively low temperature sample stream into a relatively high temperature vaporization zone through which a carrier gas is flowing comprising a sample block having inlet and outlet ports for the sample stream and a sample flow channel portion therebetween, a tubular closed end syringe member having an aperture in the side thereof immediately adjacent its closed end and a plunger selectively movable toward and away from said closed end to draw fluid samples of a predetermined volume into said syringe through said aperture, packing and guiding means in said sample block to guide the movement of said tubular syringe member on opposite sides of said sample flow channel and prevent leakage, means for partially withdrawing said plunger while said syringe aperture is in the flow channel to collect a measured volume of sample, means to move said syringe and withdrawn plunger together into said vaporization zone, means to force said plunger toward said closed end to expel all of said measured sample into said vaporization zone, means to return said syringe and plunger to its original position, means to heat said vaporization zone to a temperature of at least 450° F., means to fixedly mount said vaporization zone closely adjacent to and in closed communication with said sample block and in axial alignment with the path of movement of said syringe member while insulating it so that when the temperature of all surface areas in the vaporization zone which contact the sample vapor is greater than 450° F. the temperature in the sample block will not exceed about 400° F., said vaporization zone being contained within an enlarged cross-sectioned portion of a heat conductive member, said member being joined to said sample block by a portion of reduced cross-section, and thermal insulation means surrounding said member along a portion thereof which is intermediate said portion of enlarged cross-section and said sample block.

2. The injection system of claim 1 wherein said heating means heats said vaporization zone to a temperature of at least 600° F. while said sample block is insulated to remain at a temperature no greater than 400° F.

3. The injection system of claim 1 wherein said heating means heats said vaporization zone to a temperature of at least 625° F. while said sample block is insulated to remain at a temperature no greater than 250° F.

4. The injection system of claim 1 wherein said vaporization zone is confined within a tubular member which has a reduced diameter lower end portion which is threadedly mated and sealed to the upper portion of the sample block.

5. The injection system of claim 4 wherein said means to heat said vaporization zone surrounds only the upper portion of said tubular member positioned above said lower end portion.

6. The injection system of claim 5 wherein an insulating sleeve is positioned around the portion of the reduced diameter lower end portion which is immediately above the sample block.

7. The injection system of claim 4 wherein said tubular member is a composite which includes a hollow inner tubular portion, the outer periphery of said inner tubular portion contacting the inner diameter of an outer tubular portion and having spiral groove means by which a carrier gas is carried to the vaporization zone, the inner diameter of said inner tubular portion being spaced from the outer diameter of the syringe member when the latter is positioned therein to define a small annular channel into which the fluid sample is ejected.

8. The injection system of claim 1 wherein at least the packing and guiding means which prevents leakage between the sample flow channel and the vaporization zone comprises a fluorocarbon resin.

9. The injection system of claim 8 wherein said fluorocarbon resin is polytetrafluoroethylene.

10. The injection system of claim 8 wherein said packing and guiding means comprises a pair of spaced sealing and guiding members positioned in a metal sided chamber and compressed into contact with axially spaced end walls thereof by a resilient spring member.

11. The injection system of claim 10 wherein the space within said metal sided chamber which is located between said pair of spaced sealing and guiding members is vented so as to provide a double block and bleed sealing arrangement.

* * * * *